(12) United States Patent
Perring et al.

(10) Patent No.: US 9,220,805 B2
(45) Date of Patent: Dec. 29, 2015

(54) CONTROL OF FEMALE BODY ODOURS

(71) Applicant: Quest International Services B.V., Naarden (NL)

(72) Inventors: Keith Douglas Perring, Kent (GB); John Martin Behan, Kent (GB); Paula Maria Cawkill, Kent (GB); Michael Gordon Evans, Kent (GB)

(73) Assignee: Givaudan S.A., Vernier (CH)

( * ) Notice: Subject to any disclaimer, the term of this patent is extended or adjusted under 35 U.S.C. 154(b) by 0 days.

(21) Appl. No.: 13/712,585

(22) Filed: Dec. 12, 2012

(65) Prior Publication Data
US 2013/0102981 A1  Apr. 25, 2013

Related U.S. Application Data

(63) Continuation of application No. 10/556,301, filed as application No. PCT/GB2004/001859 on Apr. 30, 2004, now abandoned.

(30) Foreign Application Priority Data

May 9, 2003 (GB) .................................. 0310694.5
Sep. 24, 2003 (GB) .................................. 0322355.9

(51) Int. Cl.
*A61L 15/46* (2006.01)
*A61F 13/84* (2006.01)
*A61F 13/472* (2006.01)
*A61L 15/20* (2006.01)

(52) U.S. Cl.
CPC .................. *A61L 15/46* (2013.01); *A61L 15/20* (2013.01); *A61L 2300/216* (2013.01)

(58) Field of Classification Search
CPC .... A61F 13/8405; A61L 15/46; C11B 9/0061
USPC .............................................. 512/2; 604/359
See application file for complete search history.

(56) References Cited

U.S. PATENT DOCUMENTS

| | | |
|---|---|---|
| 2,131,235 A | 9/1938 | Randall et al. |
| 4,343,783 A | 8/1982 | Hooper et al. |
| 5,501,805 A | 3/1996 | Behan et al. |

FOREIGN PATENT DOCUMENTS

EP   1 275 403   1/2003

*Primary Examiner* — Peter F Godenschwager
(74) *Attorney, Agent, or Firm* — Morgan, Lewis & Bockius LLP

(57) ABSTRACT

The invention concerns the control of female body odors, particularly odors associated with body fluids, namely products of the genito-urinary tract, such as menstrual or catamenial fluids, vaginal fluids, urine, by use of low odor compositions of fragrance materials. The composition of fragrance material includes at least 5% of one or more musks and at least 5% of one or more salicylates.

10 Claims, 1 Drawing Sheet

CONTROL OF FEMALE BODY ODOURS

FIELD OF THE INVENTION

Figure 1:
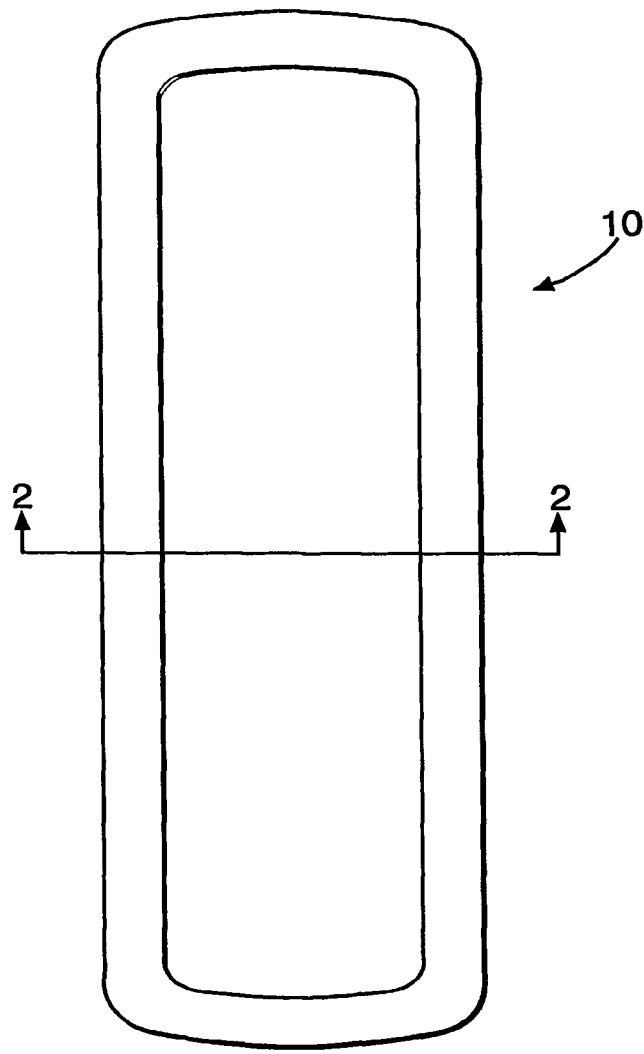

This invention concerns the control of female body odours, particularly odours associated with products of the genito-urinary tract, such as menstrual or catamenial fluids, vaginal fluids, urine. The invention relates particularly to a method of counteracting or reducing odours associated in use with an article selected from sanitary towels or napkins and panty liners, i.e. odours associated with products of the female genito-urinary tract, particularly menstrual or catamenial fluids, vaginal fluids and urine.

BACKGROUND TO THE INVENTION

EP 0404470A1 and U.S. Pat. No. 5,501,805 concern compositions of fragrance materials that have in themselves a low or imperceptible level of fragrance, i.e. a low odour intensity, yet which can confer deodorant effects in use. Such compositions may be referred to for brevity as "low odour compositions". These prior art documents disclose the use of such low odour compositions in detergent products and personal body underarm deodorant compositions (for combating axillary malodour).

It has now surprisingly been found that such low odour compositions also find use in combating other body odours.

SUMMARY OF THE INVENTION

A method of counteracting or reducing odours associated in use with an article selected from sanitary towels or napkins and panty liners, comprising providing in or on the article a composition of fragrance materials having an odour intensity index of less than about 110, the composition comprising at least 5% w/w of at least one musk and at least 5% w/w of at least one salicylate.

The invention also covers use as a material for counteracting or reducing odours associated in use with an article selected from sanitary towels or napkins and panty liners of a composition of fragrance materials having an odour intensity index of less than about 110, the composition comprising at least 5% w/w of at least one musk and at least 5% w/w of at least one salicylate.

A further aspect of the invention provides use of a composition of fragrance materials having an odour intensity index of less than about 110 in an article selected from sanitary towels or napkins and panty liners, for counteracting or reducing odours associated with female bodily fluids, the composition comprising at least 5% w/w of at least one musk and at least 5% w/w of at least one salicylate selected from a sanitary towel or napkin and a panty liner.

The invention also provides an article selected from a sanitary towel or napkin and a panty liner, wherein the article includes a composition of fragrance materials having an odour intensity index of less than about 110, the composition comprising at least 5% w/w of at least one musk and at least 5% w/w of at least one salicylate.

In all aspects of the invention, references to odour intensity index mean a value obtained by the odour intensity index method set out in EP 0404470 (based on a comparison with the odour intensity of a control sample of a 10% solution of benzyl acetate in dipropylene glycol, which corresponds to an index of 100).

It is preferred to use a composition of fragrance materials having an odour intensity index of less than about 105, more preferably less than about 100.

The composition of fragrance materials may optionally have a malodour reduction value of at least about 0.25, possibly at least about 0.5, or an odour reduction value of at least about 0.25, possibly at least about 0.5. References to malodour reduction value mean a value when tested by the procedure set out in EP 0147191; and references to odour reduction value mean a value when tested by the procedure set out in EP 0003172. EP 0404470, EP 0147191 and EP 0003172 are incorporated herein by reference.

It is to be understood that in this specification, expression such as 'perfume' and 'fragrance' extend to compositions of which the odour intensity may be so low as to be imperceptible in use.

By using a low odour composition, the present invention can enable undesirable body odours to be counteracted or reduced in a discrete manner without providing an overt fragrance that, while possibly pleasant in itself, might also be considered by the user to be undesirable, particularly given the current trend for providing fragrance-free products.

Examples of suitable perfumery materials for incorporation into a composition of fragrance materials for use in the invention (i.e. a low odour composition) are given in EP 0404470 and U.S. Pat. No. 5,501,805. In general, any of a wide range of perfumery materials may be incorporated into the compositions, provided that the basis of selection is such as to provide a deodorant effect, and the odour intensity index of the resulting composition is as defined above.

Extensive directions for the selection of materials in order to provide a deodorant effect are given for example in EP 0147191, EP 0003172, and U.S. Pat. No. 4,304,679, all three documents being incorporated herein by reference.

It is helpful if the bulk of the individual ingredients chosen for the composition also individually possess an odour intensity index less than about 110, preferably less than about 100, or even lower. Small quantities of more intense materials may, however, be tolerated, e.g. for the purpose of adjusting the mild perfume note which may be given by the overall composition.

The composition comprises at least 5% w/w, preferably at least 10% w/w, more preferably at least 20% w/w of at least one musk, based on the total weight of the composition (including any solvents). Where one or more musks are present, either in these or in other amounts, they can usefully be selected from musks such as those listed below:

| Trademark or Trivial Name: | Generic name: |
|---|---|
| Ambrettolide | Cyclohexadecen-7-olide |
| Celestolide (IFF) | 4-Acetyl-6-tert-butyl-1,1-dimethylindane |
| Dihydroambrettolide | Cyclohexadecanolide |
| Ethylene brassylate | cyclo-1,13-ethylenedioxy-tridecan-1,13-dione |
| Exaltolide (F) | Cyclopentadecanolide |
| Exaltone (F) | Cyclopentadecanone |
| Habanolide (F) | 1-oxa-5(6)-cyclohexadecen-16-one |
| Galaxolide (IFF) | 1,3,4,6,7,8-hexahydro-4,6,6,7,8,8-hexamethylcyclopenta-2-benzopyran |
| Moskene (GIV) | 1,1,3,3,5-Pentamethyl-4,6-dinitroindane |
| Musk ambrette | 2,4-dinitro-3-methyl-6-tert-butylanisole |
| Musk Ketone | 4-tert-butyl-3,5-dinitro-2,6-dimethylacetophenone |
| Musk MC4 (SA) | Ethylene 1,12-dodecanedioate |
| Musk R1 (Q) | 11-Oxahexadecanolide |
| Musk tibetine | 2-tert-butyl-1,3-dinitrol-4,5,6-trinitrobenzene |
| Musk xylol | 1-tert-butyl-3,5-dimethyl-2,4,6- |

-continued

| Trademark or Trivial Name: | Generic name: |
|---|---|
|  | trinitrobenzene |
| Phantolide (PFW) | 5-Acetyl-1,1,2,3,3,6-hexamethylindane |
| Tonalid (PFW) | 1,1,2,4,4,7-Hexamethyl-6-acetyl-1,2,3,4-tetrahydronaphthalene |
| Traseolide | 6-acetyl-1-isopropyl-2,3,3,5-tetramethylindane |
| Versalide (PFW) | 1,1,4,4-tetramethyl-6-acetyl-7-ethyl-1,2,3,4-tetrahydronaphthalene |

Suppliers indicated in brackets above are, as follows:
F=Firmenich
GIV=Givaudan
IFF=International Flavours & Fragrances
PFW=Polak's Frutal Works
SA=Soda Aromatics
Q=Quest International Preferred musks include cyclohexadecanolide, cyclopentadecanone, ethylene brassylate, ethylene dodecanedioate and musk R1.

The quantity of musk will generally not exceed 70%, more likely not exceed 60% by weight so that other (non-musk) perfume components provide at least 30% more likely at least 40% by weight of the total weight of the perfume composition (including any solvents).

The composition comprises at least 5% w/w, preferably at least 10% w/w of at least one salicylate, preferably salicylates of aliphatic or arylaliphatic alcohols containing at least three carbon atoms notably 3 to 10 carbon atoms. The amount of salicylate is based on the total weight of the composition, including any solvents. Possible salicylates include:
 amyl salicylate
 isoamyl salicylate
 isobutyl salicylate
 cis-3-hexenyl salicylate
 hexyl salicylate
 cyclohexyl salicylate
 benzyl salicylate
 phenylethyl salicylate
 propyl salicylate
 isopropyl salicylate Preferred salicylates include benzyl salicylate, cis-3-hexenyl salicylate, cyclohexyl salicylate, hexyl salicylate and phenylethyl salicylate.

It is also preferred that the composition contains at least 5% w/w, more preferably at least 10% w/w, most preferably at least 20% w/w of other perfume ingredients which are neither musk nor salicylate nor solvent that is odourless or substantially odourless, based on the total weight of the composition.

It is thus preferred to use a composition of fragrance materials comprising (a) an amount of at least 5% w/w of at least one musk, based on the total weight of the composition, (b) at least 5% of at least one salicylate, based on the total weight of the composition, and (c) at least 5% of other fragrance materials (possibly including odiferous solvents) which are neither musk nor salicylate nor odourless or substantially odourless solvent, based on the total weight of the composition.

The musk and salicylate materials are conveniently selected from the lists given above.

Perfumery solvents with no odour or with very low odour (referred to as odourless or substantially odourless) may be optionally included up to a limit of 80% by weight. Typical perfumery solvents include diethyl phthalate, dipropylene glycol, triacetin, benzyl benzoate, triethyl citrate, Hercolyn D (TM Hercules), isopropyl myristate and acetyl tributylcitrate. In some cases it may be desirable or appropriate to include odiferous perfumery solvent or solvents in small quantity.

Preferred musks and salicylates are listed in Table 1 below, which also includes preferred ingredients with low odour which may usefully be employed.

TABLE 1

| COMPONENT | CATEGORY | | |
|---|---|---|---|
|  | MUSK | SALICYLATE | OTHER |
| ACETYL CEDRENE |  |  | 1 |
| BENZYL ALCOHOL |  |  | 1 |
| BENZYL CINNAMATE |  |  | 1 |
| BENZYL SALICYLATE |  | 1 |  |
| CINNAMIC ALCOHOL |  |  | 1 |
| CINNAMYL CINNAMATE |  |  | 1 |
| cis-3-HEXENYL SALICYLATE |  | 1 |  |
| CYCLOHEXADECANOLIDE | 1 |  |  |
| CYCLOHEXYL SALICYLATE |  | 1 |  |
| CYCLOPENTADECANONE | 1 |  |  |
| ETHYLENE BRASSYLATE | 1 |  |  |
| FLOROSA (TM) (Quest) |  |  | 1 |
| GERANYL PHENYLACETATE |  |  | 1 |
| HABANOLIDE (TM) (Firmenich) | 1 |  |  |
| HEXYL CINNAMIC ALDEHYDE |  |  | 1 |
| HEXYL SALICYLATE |  | 1 |  |
| ISOBORNYL CYCLOHEXANOL |  |  | 1 |
| ISOBUTYL BENZOATE |  |  | 1 |
| ISOBUTYL CINNAMATE |  |  | 1 |
| LINALYL BENZOATE |  |  | 1 |
| LINALYL CINNAMATE |  |  | 1 |
| MEFROSOL (TM) (Quest) |  |  | 1 |
| METHYL DIHYDROJASMONATE |  |  | 1 |
| ETHYLENE DODECANEDIOATE | 1 |  |  |
| MUSK R1 (TM) (Quest) | 1 |  |  |
| PHENOXYETHANOL |  |  | 1 |
| PHENYLETHYL PHENYLACETATE |  |  | 1 |
| PHENYLETHYL SALICYLATE |  | 1 |  |
| TETRAHYDROLINALOL |  |  | 1 |

EP 0404470 and U.S. Pat. No. 5,501,805 list many other examples of perfume materials useful in compositions for use in the invention.

It is preferred to use a composition of fragrance materials including one or more musks in an amount in the range 5 to 25% by weight and one or more salicylates in an amount in the range 5 to 20% by weight, based on the total weight of the composition (including any solvents). The composition desirably also contains other perfumery ingredients (possibly including odiferous solvents), which are neither musk, salicylate nor odourless or substantially odourless solvent, in an amount of up to 50% by weight based on the total weight of the composition. The composition desirably includes one or more solvents that are odourless or substantially odourless in an amount in the range 25 to 60% by weight, based on the total weight of the composition.

The composition of fragrance materials preferably contains at least five different components, and in practice may contain considerably more components, being formulated in known manner to give a composition with desired fragrance characteristics (of low odour intensity). Examples of preferred compositions are given in the Examples below. Reference is also made to the Examples of EP 0404470 and U.S. Pat. No. 5,501,805.

The composition of fragrance materials may be in encapsulated form, for improved storage stability, e.g. at high temperatures, and to reduce odour impact prior to use. Preferred encapsulates are water-sensitive, being designed to release their contents on exposure to water. Suitable encapsulating material and techniques are well known to those skilled in the art, with suitable materials including starches and cyclodextrins: see e.g. U.S. Pat. No. 5,102,564, "Textile materials with fixed cyclodextrins as a fragrance depot", Hans-Jurgen Buschman et al, Perv. Flav., vol 27 May/June 2002, pages 36-38, and U.S. Pat. No. 5,425,887.

The sanitary towel or napkin or panty liner is intended for use by female humans, being for use external of the body, and typically comprises a liquid-absorbent pad for absorbing products of the genito-urinary tract such as menstrual or catamenial fluids, vaginal fluids, urine.

The composition of fragrance materials is conveniently absorbed in the liquid-absorbent pad of such an article.

The article is generally a disposable article, intended for single use only.

The article may otherwise be of generally conventional construction and materials, e.g. as disclosed in EP 1088536, WO 00/51657, WO 00/51652 and WO 00/67688.

The sanitary towel or napkin or panty liner typically comprises an absorbent core (constituting a liquid-absorbent pad) sandwiched between an upper layer of material, known as a top sheet, and a lower layer of material, known as a back sheet. The article may include one or more layers of liquid-impervious barrier material, in known manner.

The top sheet is of material that is permeable to fluids, to allow passage of menstrual fluid, urine etc towards the absorbent core, while keeping fluid away from the user's body. The top sheet may comprise one or more layers of material, and is typically made of woven or non-woven fabrics or films, e.g. a sheet of perforated plastics film etc.

The back sheet, or one or more layers of barrier material, functions to prevent fluids absorbed by the absorbent core from passing through the article and leaking onto adjacent garments of a user. The back sheet is thus usually impervious to fluids, and is commonly made of a thin, unperforated film of plastics materials e.g. polyethylene film. The back sheet and top sheet are typically of greater extent than the absorbent core, with peripheral portions of the two sheets secured together to retain the core therebetween. The back sheet at least may extend further laterally, to form side flaps or "wings". Adhesive material is usually applied to the outer face of the back sheet, to permit temporary attachment of the article to the clothing of a user.

The absorbent core functions to absorb and contain fluid and commonly comprises natural, modified or synthetic fibres, particularly modified or non-modified cellulose fibres in the form of fluff and/or tissues, or textile fibres such as rayon or polyester. The core may additionally include a super-absorbent material, usually a gelling material such as sodium polymethacrylate.

Further details of known articles of this sort can be found, e.g. in WO 00/51657 and EP 1088536.

The composition of fragrance materials is conveniently absorbed into the absorbent core of such articles, e.g. by being applied to the core during manufacture of the article. The composition may additionally or alternatively be present in different parts of the article, e.g. being applied to one or both of the major faces of the core.

The composition of fragrance materials is used in an appropriate amount to obtain the desired effect in any given application. Suitable amounts can be readily determined by experiment. The composition is typically present in an amount in the range 2 to 50 mg per article, preferably 5 to 30 mg per article, more preferably 10 to 20 mg per article.

The composition of fragrance materials is found to be particularly effective in overcoming or reducing malodours resulting from amine compounds, such as trimethylamine, known sometimes to be present in products of the genito-urinary tract.

Figure 2:
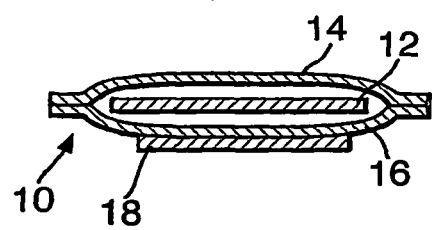

The invention will be further described, by way of illustration, in the following Examples and with reference to the accompanying drawings, in which:

FIG. 1 is a schematic plan view of a sanitary towel in accordance with the invention; and FIG. 2 is a schematic sectional view (not to scale) of the sanitary towel of FIG. 1 taken along line 2-2 of FIG. 1.

DETAILED DESCRIPTION OF THE DRAWINGS

Referring to the drawings, there is illustrated a sanitary towel 10 which comprises an absorbent core 12 sandwiched between a top sheet 14 and a back sheet 16. The core 12 comprises cellulosic fibres, and is generally rectangular in plan, with rounded corners, having a maximum length of about 200 mm and a maximum width of about 70 mm. The top sheet 14 comprises a hydrophobic, liquid permeable apertured film. The back sheet 16 comprises a waterproof polyethylene film. The top sheet 14 and back sheet 16 are both generally rectangular in plan, with rounded corners, having a maximum length of about 230 mm and a maximum width of about 90 mm. Edge portions of the top sheet and bottom sheet extending beyond the core 12 are adhered together. A rectangular patch of adhesive material 18, about 170 mm long and about 50 mm wide, is provided on the outer face of the back sheet, for temporarily adhering the towel 10 to the underwear of a user.

In accordance with the invention, a composition of fragrance materials comprising at least 5% w/w of at least one musk and at least 5% w/w of at least one salicylate and having an odour intensity index of less than about 110 is applied to the material of core 12 in an amount in the range 2 to 40 mg, to be absorbed by the core 12, prior to manufacture of the towel 10. The composition is conveniently as specified in one of the following Examples.

Example 1

Table 2 below gives the composition of 5 preferred compositions of fragrance materials for use in accordance with the present invention, with composition E being particularly favoured.

| COMPONENT | | w/w % | | | | |
| --- | --- | --- | --- | --- | --- | --- |
| | | A | B | C | D | E |
| ACETYL CEDRENE | | 3.5 | | | 0.5 | |
| BENZYL CINNAMATE | | 0.5 | | | | |
| BENZYL SALICYLATE | Sa | 4 | | | | |
| CINNAMIC ALCOHOL | | 0.2 | | | | |
| CINNAMYL CINNAMATE | | | | 0.5 | | |
| cis-3-HEXENYL SALICYLATE | Sa | | | 4.5 | 0.5 | |
| CYCLOHEXADECANOLIDE | M | 4.5 | | 5.5 | | |
| CYCLOHEXYL SALICYLATE | Sa | | | 1.5 | | |
| CYCLOPENTADECANONE | M | 4.5 | | 5.5 | | |
| DIPROPYLENE GLYCOL | S | | 4 | 0.6 | | 1.6 |
| DISPIRONE (TM) (Quest) | | | | 0.1 | | 0.2 |
| ETHYLENE BRASSYLATE | M | | 6.5 | | 15.7 | 5 |
| ETHYLENE DODECANEDIOATE | M | | | 12.3 | | |
| FLOROSA (TM) (Quest) | | | 5.5 | 0.1 | 0.5 | 0.2 |
| GERANYL PHENYLACETATE | | | 0.4 | | | |
| HABANOLIDE (TM) (Firmenich) | M | | 2.5 | | | 3 |

-continued

| COMPONENT | | w/w % | | | | |
|---|---|---|---|---|---|---|
| | | A | B | C | D | E |
| HEXYL SALICYLATE | Sa | 8 | 6 | 4 | 15 | 5 |
| ISOBORNYL CYCLOHEXANOL | | 1.5 | | 0.7 | | 0.5 |
| ISOBUTYL BENZOATE | | | 1.5 | | | |
| ISOBUTYL CINNAMATE | | | | 0.1 | | |
| ISOPROPYL MYRISTATE | S | 52 | | 59 | 12.5 | |
| LINALYL BENZOATE | | | | 1.5 | | |
| LINALYL CINNAMATE | | | 0.5 | | | |
| MEFROSOL (TM) (Quest) | | 2.2 | | 0.5 | 1.3 | 1 |
| METHYL DIHYDROJASMONATE | | | 15 | 2.0 | 25 | 20 |
| MUSK R1 (TM) (Quest) | M | 1.5 | | 1.2 | | |
| PHENOXYETHANOL | | 5.5 | 12 | | 14 | 15 |
| PHENYLETHYL PHENYLACETATE | | 1.5 | | 0.5 | | |
| PHENYLETHYL SALICYLATE | Sa | 3.6 | | | | |
| TETRAHYDROLINALOL | | | | | 2.5 | 0.5 |
| TRIACETIN | S | | | | 12.5 | |
| TRIETHYL CITRATE | S | | 53 | | | 48 |
| TOTAL | | 100 | 100 | 100 | 100 | 100 |
| % Musk | | 10.5 | 9 | 24.5 | 15.7 | 8 |
| % Salicylate | | 15.6 | 6 | 10 | 15.5 | 5 |
| % Other | | 21.9 | 28 | 5.9 | 43.8 | 37.4 |
| % Solvent | | 52 | 57 | 59.6 | 25 | 49.6 |

Note:
Sa = Salicylate
M = Musk and
S = Solvent

Perfume compositions A to E have an odour intensity index of less than 110.

Example 2

The perfumes of the invention may be assessed using standard malodour intensity assessment methods wherein malodour and counteractant may interact only in the gas phase or in the nose. Any reduction of malodour perception will occur primarily through sensory interactions (other mechanisms will of course be feasible in the case of intimate mixing of malodour and counteractant).

1 ml fragrance E in Example 1 was placed into a 15 ml jar and this was placed into a 500 ml jar alongside a similar jar containing 3 ml of a malodour model (0.1% w/w solution in diethyl phthalate of hexylamine).

The samples were assessed against a control containing malodour alone. The samples were randomised and coded and were olfactorily assessed by trained sensory panellists employing magnitude estimation techniques. The results were analysed using Analysis of Variance and multiple comparison techniques.

| Malodour intensity: | Perfume E: | LSMEAN SCORE = 25 |
|---|---|---|
| | Control: | LSMEAN SCORE = 48 |

The malodour intensity was reduced by about 50%.

The invention claimed is:

1. A method of counteracting or reducing odours associated in use with an article selected from sanitary towels or napkins and panty liners, comprising providing in or on the article a composition of fragrance materials having an odour intensity index of less than about 110, the composition comprising:
   at least 5% w/w of at least one musk selected from the group consisting of cyclohexadecanolide (dihydroambrettolide); cyclopentadecanone; cyclo-1,13-ethylenedioxy-tridecan-1,13-dione (ethylene brassylate); 11-oxahexadecanolide; ethylene 1,12-dodecanedioate; 1-oxa-5(6)-cyclohexadecen-16-one and cyclopentadecanolide;
   at least 5% w/w of at least one salicylate; and
   at least 25% to 60% of one or more odourless or substantially odourless solvents selected from the group consisting of triacetin, triethyl citrate and isopropyl myristate.

2. The method according to claim 1, wherein the composition of fragrance materials has an odour intensity index of less than about 105.

3. The method according to claim 1, where the composition of fragrance materials comprises at least 10% w/w of at least one musk, based on the total weight of the composition.

4. The method according to claim 1, wherein the at least one musk is selected from the group consisting of: cyclo-1,13-ethylenedioxy-tridecan-1,13-dione, cyclopentadecanolide and 1-oxa-5(6)-cyclohexadecen-16-one.

5. The method according to claim 1, wherein the at least one salicylate is selected from the group consisting of: benzyl salicylate, cis-3-hexenyl salicylate, cyclohexyl salicylate, hexyl salicylate and phenylethyl salicylate.

6. The method according to claim 1, wherein the composition of fragrance materials contains at least 5% w/w of other perfume ingredients which are neither musk nor salicylate nor solvent that is odourless or substantially odourless, based on the total weight of the composition.

7. An article selected from a sanitary towel or napkin and a panty liner, wherein the article includes a composition of fragrance materials having an odour intensity index of less than about 110, the composition comprising:
   at least 5% w/w of at least one musk selected from the group consisting of cyclohexadecanolide (dihydroambrettolide); cyclopentadecanone; cyclo-1,13-ethylenedioxy-tridecan-1,13-dione (ethylene brassylate); 11-oxahexadecanolide; ethylene 1,12-dodecanedioate; 1-oxa-5(6)-cyclohexadecen-16-one and cyclopentadecanolide;
   at least 5% w/w of at least one salicylate; and
   at least 25% to 60% of one or more odourless or substantially odourless solvents selected from the group consisting of triacetin, triethyl citrate, and isopropyl myristate.

8. The article according to claim 7, comprising a liquid-absorbent pad for absorbing female bodily fluids comprising products of the genito-urinary tract.

9. The article according to claim 8, wherein the composition of fragrance material is absorbed in the liquid-absorbent pad of the article.

10. The article according to claim 9, wherein the article is a disposable article, intended for single use only.

* * * * *

UNITED STATES PATENT AND TRADEMARK OFFICE
CERTIFICATE OF CORRECTION

PATENT NO.       : 9,220,805 B2
APPLICATION NO.  : 13/712585
DATED            : December 29, 2015
INVENTOR(S)      : Keith Douglas Perring et al.

It is certified that error appears in the above-identified patent and that said Letters Patent is hereby corrected as shown below:

On the Title Page:
(71) Applicant: delete "Quest International Services B.V., Naarden (NL)" and insert --Givaudan S.A., Vernier (CH)--

Signed and Sealed this
Twenty-third Day of August, 2016

Michelle K. Lee
*Director of the United States Patent and Trademark Office*